United States Patent [19]

Geithman et al.

[11] 4,111,053
[45] Sep. 5, 1978

[54] AUDIBLE BOND TESTER

[75] Inventors: Glenn Allen Geithman, Renton; Wayne Earl Woodmansee, Seattle, both of Wash.

[73] Assignee: The Boeing Company, Seattle, Wash.

[21] Appl. No.: 809,872

[22] Filed: Jun. 24, 1977

[51] Int. Cl.² .......................................... G01N 29/00
[52] U.S. Cl. .................................... 73/588; 73/609
[58] Field of Search ................ 73/582, 583, 588, 610, 73/609, 628, 574, 579, 150 A

[56] References Cited

U.S. PATENT DOCUMENTS

| 2,846,874 | 8/1958 | Horn | 73/588 |
| 3,504,532 | 4/1970 | Muenow et al. | 73/579 |
| 3,813,926 | 6/1974 | Stubbeman | 73/609 |
| 3,930,404 | 1/1976 | Ryden, Jr. | 73/610 X |
| 4,008,602 | 2/1977 | Love | 73/609 |

Primary Examiner—Jerry W. Myracle
Attorney, Agent, or Firm—Conrad O. Gardner; B. A. Donahue

[57] ABSTRACT

A system for inspection of adhesively bonded structures utilizing a piezoelectric transmitting transducer for transmitting a fixed frequency tone burst, e.g., 25 KHz, at a predetermined repetition rate, e.g., 100 Hz, into a part being tested and including a piezoelectric receiving transducer also coupled to the part for providing in a receiver circuit an audible output which permits the operator to distinguish amplitude variations of the 100 Hz repetition rate signal representative of the presence of an unbonded area.

3 Claims, 3 Drawing Figures

AUDIBLE BOND TESTER

This invention relates to the inspection of materials by means of ultrasonic waves and more particularly, adhesively bonded aircraft structures of a "stiff" nature, e.g., honeycomb and aluminum type structures, as contrasted to structures of a "complaint" nature, such as fiber glass.

Heretofore, ultrasonic work piece thickness inspection has been performed as exemplified in U.S. Pat. No. 3,050,989 by transmitting a frequency and amplitude modulated tone burst into the test article with variations in amplitude of the internal vibration of the test article being detected and displayed on an oscilloscope as representative of the thickness of the test article. Further representative of the prior art is U.S. Pat. No. 2,918,621, wherein audible signals are utilized to indicate the presence of flaws detected by a magnetic flaw detection apparatus, and U.S. Pat. No. 3,361,225, further illustrative of audible bond testing.

In contrast, the present system utilizes transmitting and receiving circuits for generating and processing 25 KHz tone bursts having a 100 Hz repetition rate for providing optimum system performance for detecting flaws producing high mechanical impedance changes at about the system operating frequency of 25 KHz.

It is accordingly an object of this invention to provide a system including receiving and transmitting circuits operating at a frequency of 25 KHz with a 100 Hz repetition rate for detecting flaws producing a high mechanical impedance change around about the operating frequency of 25 KHz such as in structures with stiff face sheets, e.g., aluminum brazed titanium and adhesively bonded honeycomb.

Other objects and advantages will become apparent from the following description taken in conjunction with the accompanying drawing in which.

Figure 1:
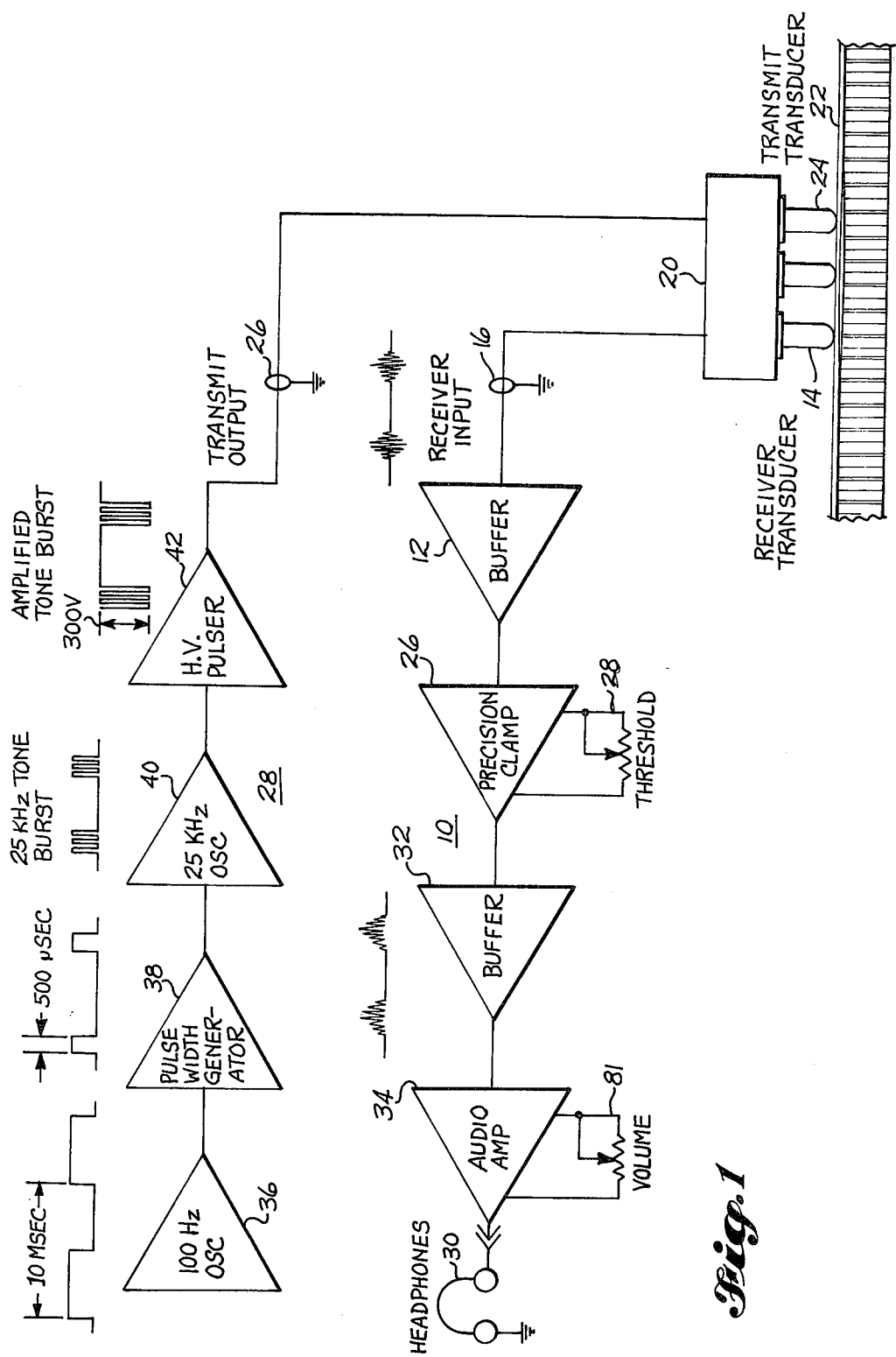
FIG. 1 is a block diagram of an embodiment of the present ultrasonic non-destructive bond inspection system.
Figure 3:
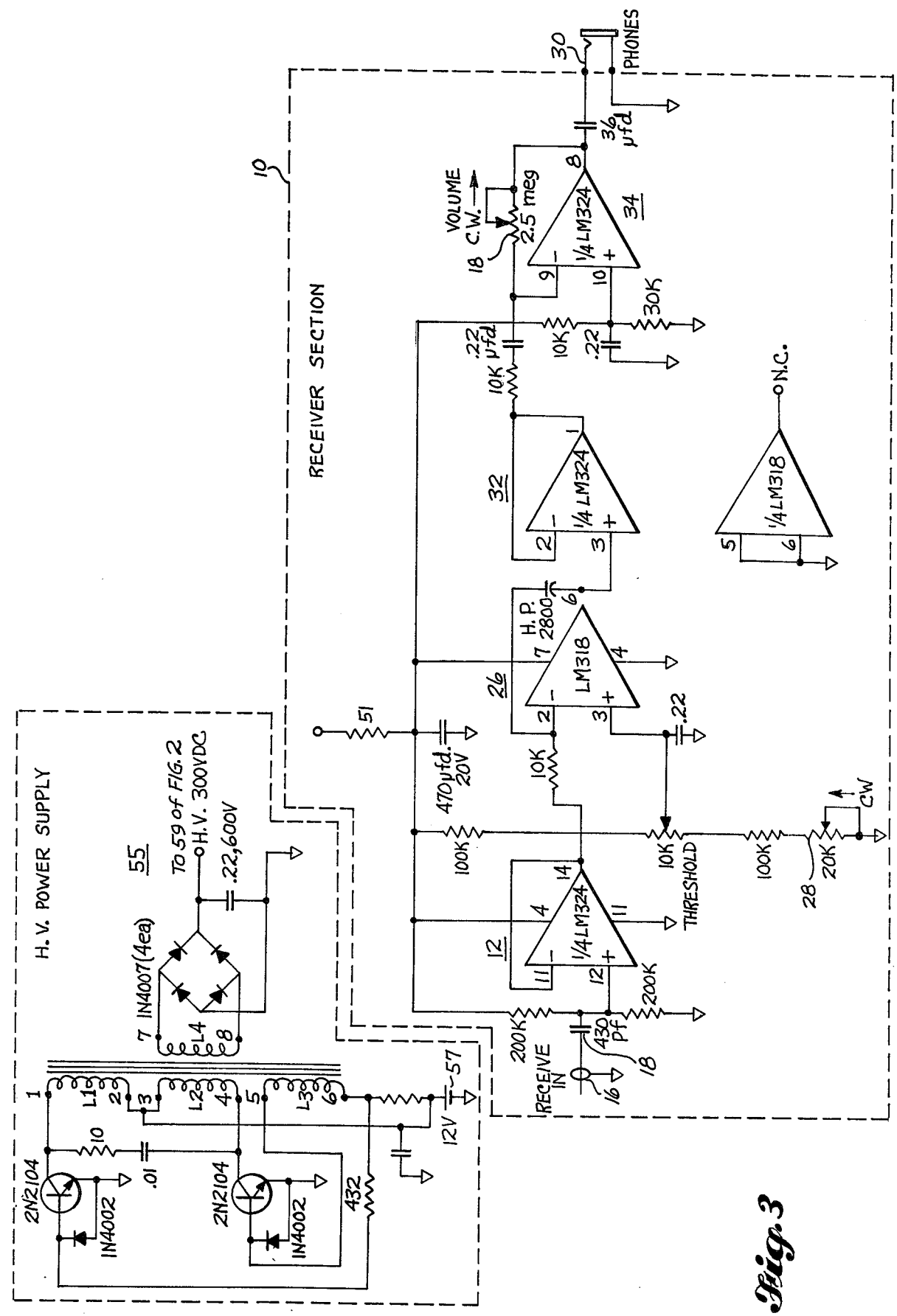
FIG. 3 is a detailed schematic circuit diagram of the receiver portion of the system shown in FIG. 1 including an inverter circuit for providing high voltage to the pulser circuit shown in FIG. 2.

Turning now to the system of FIG. 1, it will be noted from the functional block diagram that the receiving channel 10 (shown in detailed schematic form in FIG. 3) utilizes a buffer stage 12 (shown as a unity gain buffer amplifier 12 in FIG. 3) coupled to receive a 25 KHz signal from piezoelectric receiver transducer 14 connected to receiver input terminal 16. In FIG. 3 it can be seen that coupling of the input signal from input terminal 16 to unity gain buffer amplifier 12 is through 430 pf capacitor 18, which value of capacitance is selected to accept the aforementioned 25 KHz system operating frequency signal while providing rejection of lower frequency undesired audio frequency signals which result from sliding of the probe housing 20 along the surface of the structure 22 being inspected. Cylindrical probe housing 20 also includes piezoelectric transmitter trasducer 24 which is coupled to output terminal 26 of transmitting channel 28. Cylindrical probe housing 20 physically coupled by direct contact with structure 22 may be obtained and housing receiver transducer 14 and transmitter transducer 24 may comprise a type No. 57A8805 manufactured by the Automation Industries Co. of Danbury, Conn.

The output of buffer stage 12 of receiver 10 is coupled to clamping circuit 26, which includes a variable potentiometer 28 for establishing a threshold control so that signals below a preset amplitude level can be rejected by the operator wearing headphones 30 at the output of receiving channel 10. A third stage, comprising buffer amplifier 32 (seen in detailed schematic of FIG. 3 as a unity gain buffer amplifier), is coupled to the output of clamping circut 26 to provide isolation while a subsequent stage comprising audio amplifier circuit 34 provides sufficient audio output power for driving an audio output device (headphones 30 as shown in FIG. 1).

Figure 2:
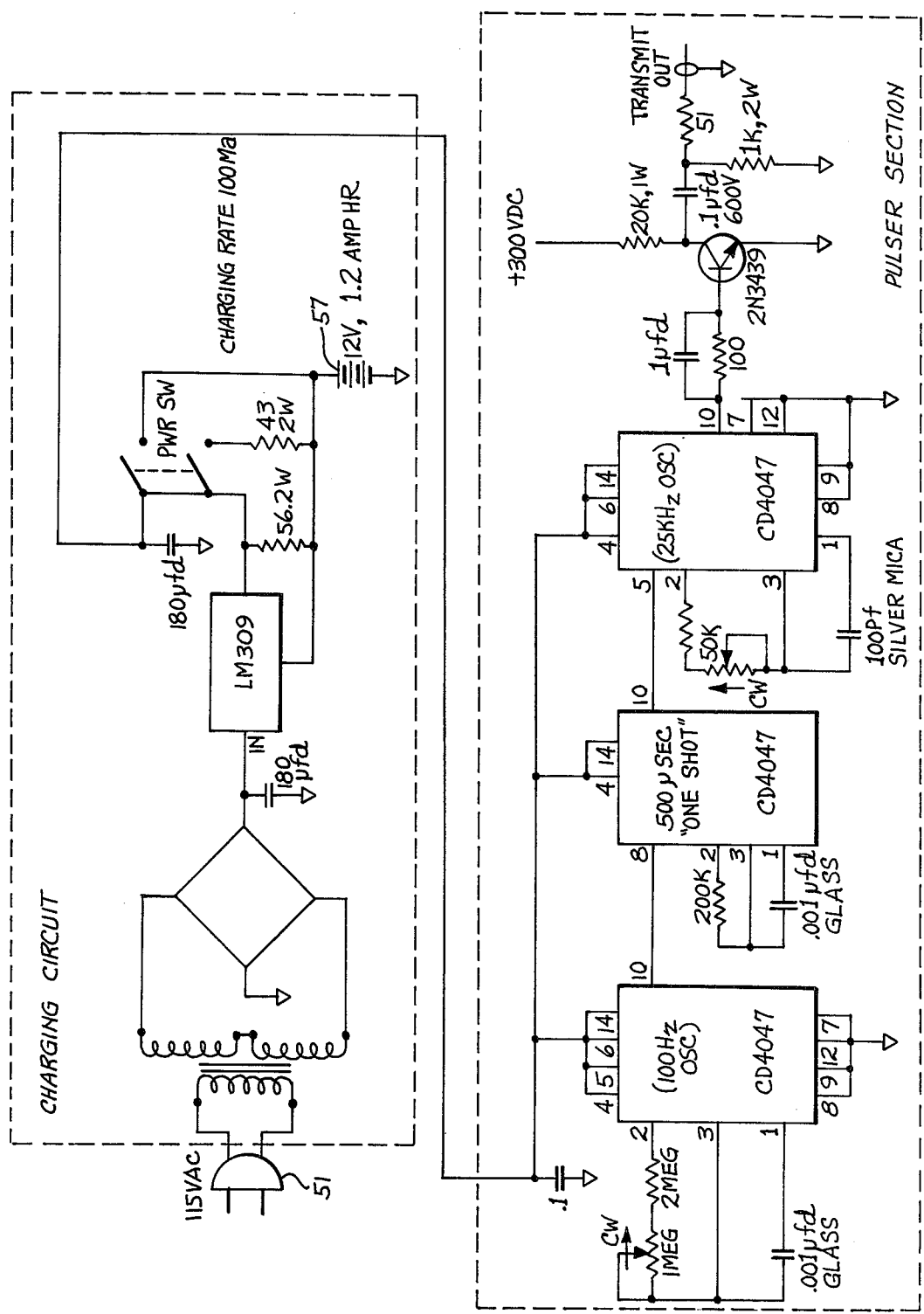
FIG. 2 is a detailed schematic circuit diagram of the transmitter portion of the system shown in FIG. 1 including charging circuit for the pulser circuit.

Turning now to transmitting channel 28, it will be noted that a first stage 100 Hz oscillator 36 comprises as seen in the detailed schematic of FIG. 2, an astable multivibrator circuit. The output of 100 Hz oscillator circuit 36 is coupled to pulse width generator 38 firing "one shot" as seen in FIG. 2, thereby generating 500 microsecond pulses. The output 500 microsecond pulses from pulse width generator circut 38 are coupled to drive the third stage, comprising 25 KHz oscillator circuit 40, which provides one hundred 25 KHz tone bursts per second. A further and final stage in transmitter channel 28 comprises high voltage pulser 42 which functions as a high voltage switching means for driving by way of output terminal 26 the transmitter transducer 24 of probe housing 20 of FIG. 1.

A power supply 49 shown in FIG. 2 provides 12 volts D.C. for stages 36, 38, and 40 in transmitter channel 28 from a source 57, comprising 12 "C" size nickel cadmium cells, which supply 49 also includes an internal charging circuit powered from 115 A.C. at connector 51, thereby allowing power supply 49 to be charged, whether the present system is in operating condition or turned off.

High voltage power supply 55 of FIG. 3 is an inverter circuit for providing high voltage (300 V.D.C.) from 12 V.D.C. source 57, suitable for powering high voltage pulser circuit 42 at terminal 59 thereof (of FIG. 2).

During system operation and with headphones 30 prepared for listening, the operator adjusts volume control 81 to predetermined amplitude level (usually a level where no noise is obtained when scanning a major portion of the surface of the structure being inspected) and with a light steady pressure moves probe 20 along and in contact with the surface of structure 22 being inspected for flaws in the bonded surface. As probe 20 is scanned across structure containing a disbond, the reduced impedance of the faulty area causes the test surface to vibrate at 25 KHz with a greater amplitude than adjacent, properly bonded portions of the structure. The increased vibrational amplitude of the surface couples a larger 25 KHz tone burst from transmitting transducer 24 to receiving transducer 14. When the 25 KHz vibrations detected at receiving transducer 14 exceed the threshold setting of clamping circuit 26, an audible 100 Hz signal at the burst repetition frequency is amplified and coupled to headset 30. As the inspector scans over a disbond, the audible 100 Hz tone identifies the faulty area. Use of an audible flaw indication allows the inspector to concentrate on moving probe 20 in a systematic scan pattern to obtain thorough coverage of a part without the distraction of having to simultaneously watch a meter to detect flaws.

We claim:

1. Apparatus for ultrasonic inspection of a work piece comprising:

receiving and transmitting piezoelectric transducer elements adapted to be positioned in accoustically coupled relationship to the work piece;

a fixed frequency tone modulated transmitting circuit for providing 25 KHz tone bursts at about a 100 Hz repetition rate connected to energize said transmitting piezoelectric transducer element; and, receiver circuit means connected to said receiving piezoelectric transducer element for providing an audio output signal at said tone burst repetition frequency of about 100 Hz and proportional to the 25 Hz signal sensed by said receiving piezoelectric transducer element.

2. Apparatus for ultrasonic inspection of a work piece comprising:

receiving and transmitting piezoelectric transducer elements adapted to be positioned in accoustically coupled relationship to the work piece;

a fixed frequency tone modulated transmitting circuit for providing tone bursts at a predetermined ultrasonic frequency at a constant repetition rate having a frequency less than said predetermined ultrasonic frequency, said transmitting circuit connected to energize said transmitting piezoelectric transducer element and vibrate said work piece at said predetermined ultrasonic frequency; and, receiver circuit means connected to said receiving piezoelectric transducer element for providing an audio output signal at the tone burst repetition frequency having an amplitude level responsive to detection of a flaw condition in said work piece.

3. The apparatus of claim 2 wherein said fixded frequency tone modulated transmitting circuit comprises a 100 Hz oscillator circuit coupled to a pulse width generator circuit, said pulse width generator circuit coupled to a 25 KHz oscillator circuit having an output coupled to a high voltage pulser circuit, said high voltage pulser circuit having an output terminal connected to said transmitting piezoelectric transducer element.

* * * * *